United States Patent
Smith et al.

(10) Patent No.: US 10,237,664 B2
(45) Date of Patent: Mar. 19, 2019

(54) AUDIO LOGGING FOR PROTECTED PRIVACY

(71) Applicant: Cochlear Limited, Macquarie University (AU)

(72) Inventors: Zachary Mark Smith, Greenwood Village, CO (US); Harish Krishnamoorthi, Englewood, CO (US)

(73) Assignee: Cochlear Limited, Macquarie University (AU)

( * ) Notice: Subject to any disclaimer, the term of this patent is extended or adjusted under 35 U.S.C. 154(b) by 51 days.

(21) Appl. No.: 15/159,630

(22) Filed: May 19, 2016

(65) Prior Publication Data

US 2017/0171671 A1 Jun. 15, 2017

Related U.S. Application Data

(60) Provisional application No. 62/264,948, filed on Dec. 9, 2015.

(51) Int. Cl.
*A61N 1/36* (2006.01)
*H04R 25/00* (2006.01)

(52) U.S. Cl.
CPC ....... *H04R 25/505* (2013.01); *A61N 1/36036* (2017.08); *A61N 1/36082* (2013.01);
(Continued)

(58) Field of Classification Search
CPC .... H04R 25/505; H04R 25/30; H04R 25/554; H04R 25/558; H04R 2225/67;
(Continued)

(56) References Cited

U.S. PATENT DOCUMENTS 8,625,577 B1   1/2014  Henderson et al.
8,917,833 B1  12/2014  Henderson et al.
(Continued)

OTHER PUBLICATIONS

Cowan, "There are two word length effects in verbal short-term memory: Opposed effects of duration and complexity" (1997) Psychological Science, 8, 290-295.*
(Continued)

*Primary Examiner* — Vivian Chin
*Assistant Examiner* — Con P Tran
(74) *Attorney, Agent, or Firm* — Edell, Shapiro & Finnan, LLC (57) ABSTRACT

Disclosed herein are methods, systems, and devices for discontinuously recording audio input representative of an audio environment. The audio environment can be an environment of a recipient of a hearing prosthesis and the discontinuously recorded audio input can be used to characterize the audio environment of the recipient, to control settings of the hearing prosthesis, or to provide some other application. Discontinuously recording the audio input can provide a recording that characterizes the audio environment of the recipient while protecting the privacy of individuals speaking nearby the recipient. Discontinuously recording the audio input may include recording discontinuous time segments of the audio input such that the semantic content of speech within the audio input, the identity of speakers in the audio input, or other private information present in the audio input is masked.

27 Claims, 6 Drawing Sheets

(52) U.S. Cl.
CPC ........... *H04R 25/30* (2013.01); *H04R 25/554* (2013.01); *H04R 25/558* (2013.01); *H04R 2225/67* (2013.01)

(58) Field of Classification Search
CPC ............ A61N 1/36032; A61N 1/36036; A61N 1/36038; A61N 1/36039; A61N 1/36082
USPC ..... 381/58, 312, 73.1, 122, 317, 60; 346/30, 346/29; 369/19, 20, 63, 64, 65; 713/176, 713/168
See application file for complete search history.

(56) References Cited

U.S. PATENT DOCUMENTS

| | | | | |
|---|---|---|---|---|
| 2002/0078750 A1* | 6/2002 | Wright | .................... | A61B 5/12 73/585 |
| 2006/0109983 A1* | 5/2006 | Young | .................... | H04K 3/43 380/252 |
| 2012/0215283 A1* | 8/2012 | Chambers | .......... | A61N 1/36032 607/57 |

OTHER PUBLICATIONS

George A. Miller and J.C.R. Licklider, 'The Intelligibility of Interrupted Speech,' The Journal of the Acoustical Society of America, vol. 22 No. 2, Mar. 1950.

* cited by examiner

AUDIO LOGGING FOR PROTECTED PRIVACY

CROSS-REFERENCE TO RELATED APPLICATION

This application claims priority to U.S. Provisional Patent Application No. 62/264,948, filed Dec. 9, 2015, which is incorporated herein by reference.

BACKGROUND

Unless otherwise indicated herein, the description provided in this section is not itself prior art to the claims and is not admitted to be prior art by inclusion in this section.

Various types of hearing prostheses provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing prostheses such as hearing aids or electromechanical hearing devices. A hearing aid, for instance, typically includes at least one small microphone to receive sound, an amplifier to amplify certain portions of the detected sound, and a small speaker to transmit the amplified sounds into the person's ear. An electromechanical hearing device, on the other hand, typically includes at least one small microphone to receive sound and a mechanism that delivers a mechanical force to a bone (e.g., the recipient's skull, or middle-ear bone such as the stapes) or to a prosthetic (e.g., a prosthetic stapes implanted in the recipient's middle ear), thereby causing vibrations in cochlear fluid.

Further, people with certain forms of sensorineural hearing loss may benefit from hearing prostheses such as cochlear implants and/or auditory brainstem implants. Cochlear implants, for example, include at least one microphone to receive sound, a unit to convert the sound to a series of electrical stimulation signals, and an array of electrodes to deliver the stimulation signals to the implant recipient's cochlea so as to help the recipient perceive sound. Auditory brainstem implants use technology similar to cochlear implants, but instead of applying electrical stimulation to a person's cochlea, they apply electrical stimulation directly to a person's brain stem, bypassing the cochlea altogether, still helping the recipient perceive sound.

In addition, some people may benefit from hybrid hearing prostheses, which combine one or more characteristics of the acoustic hearing aids, vibration-based hearing prostheses, cochlear implants, and auditory brainstem implants to enable the person to perceive sound.

A hearing prosthesis may include an external unit that performs at least some processing functions and an internal stimulation unit that at least delivers a stimulus to a body part in an auditory pathway of the recipient. The auditory pathway includes a cochlea, an auditory nerve, a region of the recipient's brain, or any other body part that contributes to the perception of sound. In the case of a totally implantable medical device, the stimulation unit includes both processing and stimulation components, though an external unit may still perform some processing functions when communicatively coupled or connected to the stimulation unit.

A recipient of the hearing prosthesis may wear the external unit of the hearing prosthesis on the recipient's body, typically at a location near one of the recipient's ears. The external unit may be capable of being physically attached to the recipient, or the external unit may be attached to the recipient by magnetically coupling the external unit and the stimulation unit.

A hearing prosthesis may have a variety of settings that control the generation of stimuli based on detected sounds. Such settings can include settings of a filter bank used to filter the received audio, a gain applied to the received audio, a mapping between frequency ranges of received audio and stimulation electrodes, or other settings. Such settings can be controlled to improve a recipient's ability, based on stimuli received from the hearing prosthesis, to discern speech or to perceive some other information. For example, settings of a filter bank can be controlled to remove noise from a detected audio signal that includes speech. Such settings may be controlled based on the experience of a recipient or based on properties of an audio environment of the recipient. For example, an audiologist could control the settings based on a recipient's description of a noisy environment that caused the recipient to experience difficulty understanding speech.

SUMMARY

Hearing prostheses or other devices configured to receive audio input can be configured to record such received audio input. Recorded audio input can represent an audio environment of a user (e.g., a recipient) of the device such that the recorded audio input can be used to characterize the audio environment. Such a characterization of the audio environment can be used to control settings of the device to improve operation of the device when exposed to similar audio environments or used according to some other application. Further, the recorded audio input can include recordings of speech or other sounds generated by the user, by people speaking to the user, or by people nearby the user.

To facilitate recording of audio input that is sufficient to characterize an audio environment while helping to preserve the privacy of people whose speech is present in the audio input, the present disclosure is directed to aspects of discontinuously recording audio input. By way of example, discontinuous segments of an audio input can be recorded without recording portions of the audio input between the discontinuous time segments. The recorded discontinuous time segments can represent the audio environment (e.g., can have a spectral content similar to the audio environment) such that the recorded discontinuous time segments can be used to control settings of a device (e.g., a hearing prosthesis), to characterize the audio environment, or according to some other application. Further, omission of the portions of the audio input between the recorded discontinuous time segments can mask speech content or other content in the audio input. Such masking can protect the privacy of people whose speech or other sounds are contained in the received audio input.

The timing, duration, ordering, or other properties of the recorded discontinuous time segments can be specified to mask the information content of speech, e.g., to mask semantic content of speech, to mask the identity of a speaker, and/or to mask other private information present in speech or other sounds that are present in the received audio input.

The intelligibility and/or information content of any speech that is recorded during the discontinuous time segments can be reduced by increasing the length of time intervals between the recorded discontinuous time segments. Thus, the intervals between the time segments can be maintained greater than a specified minimum interval. For example, the time segments can be separated in time by more than approximately 800 milliseconds. Further, the intelligibility of speech can be additionally reduced by maintaining the duration of the time segments less than a specified maximum duration. Such a specified maximum duration can be less than the average duration of word of speech, that is, less than approximately 400 milliseconds. For example, the time segments can have durations that are less than approximately 200 milliseconds. Private information in the audio input can be further masked by changing the order of the discontinuously recorded time segments.

Discontinuously recorded time segments of an audio input, or information related thereto, can be output. This can include transmitting the recorded time segments between modules or components of a device, e.g., from a controller of a hearing prosthesis to a data storage of the hearing prosthesis. Additionally or alternatively, outputs based on the discontinuously recorded time segments can be provided from a device to systems or people external to the device. For instance, the discontinuously recorded time segments can be output, via a wired or wireless connection, to a server, a data storage, or some other system. In another example, discontinuously recorded time segments can be output as sound to allow an audiologist or other person to experience or evaluate the audio environment represented by the audio input. In yet another example, such discontinuously recorded time segments output as sound could be used by a recipient of a hearing prosthesis to remember a situation when the recipient experienced difficulty using their hearing prosthesis or to recall information about some other event of interest represented by the discontinuously recorded time segments. In some examples, a spectral content, noise floor, noise spectrum, or other information can also be determined based on the discontinuously recorded time segments and the determined information can be output (e.g., to a server or other system).

A variety of devices can use a microphone or other sound-detecting means to receive audio input and could discontinuously record such audio input in accordance with this disclosure. Such devices can include a hearing prosthesis, such as a hearing aid, a cochlear implant system, a brainstem stimulation implant system, an electromechanical hearing system, or some other hearing prosthesis. Alternatively, devices other than a hearing prosthesis, such as a cell phone or other electronic device worn or carried by a person (e.g., a hearing prosthesis recipient), can include a microphone and can discontinuously record audio input received using the microphone.

Moreover, audio input can be discontinuously recorded by a device that does not include a microphone or other sound-detecting means that are being used to detect the audio input. For instance, a first device can be configured to discontinuously record an audio input that a second device uses a microphone to receive and provides to the first device. As a specific example of this, an external unit of a cochlear implant system can include a microphone and can use the microphone to detect audio input. The external unit can then transmit the detected audio input, via a wired or wireless connection, to another device (e.g., a cell phone, or a body-worn controller unit). The other device can then discontinuously record time segments of the audio input received by and from the external unit.

In addition, a device that is discontinuously recording audio input can record data about events associated with the audio input. With respect to a hearing prosthesis, for instance, such events can include a threshold change in the audio environment (e.g., when a recipient enters a noisy environment), a receipt of user-input changing a setting of the hearing prosthesis (e.g., a volume setting, a filter bank setting), a receipt of user-input indicating difficulty perceiving sounds from stimuli provided by the hearing prosthesis, the hearing prosthesis automatically changing a filter bank setting, or some other events. Recorded data about such events can help to characterize the audio environment represented by the audio input, in order to help facilitate using the recorded time segments as a basis to control one or more operational settings of a hearing prosthesis, or to perform some other actions. The recorded data can include a timing of an occurrence of an event relative to the timing of one or more discontinuously recorded time segments of the audio input. Further, in some examples, a device can begin discontinuously recording audio input in response to detecting the occurrence of such an event.

Accordingly, in one respect, disclosed herein is a method operable by a system configured to detect audio input representing an audio environment. Per the method, the system receives audio input representing the audio environment, e.g., by operating a microphone. The system then discontinuously records the received audio input, with the discontinuous recording including recording discontinuous time segments of the received audio input without recording portions of the audio input between the discontinuous time segments. In turn, the system then provides an output based on the discontinuous recording.

In another respect, disclosed is a system comprising a hearing prosthesis and a controller. The hearing prosthesis is operable to receive an audio input representing an audio environment of a recipient and to stimulate a physiological system of the recipient in accordance with the received audio input. The controller is configured to discontinuously record the received audio input, with the discontinuous recording including recording discontinuous time segments of the received audio input without recording portions of the audio input between the discontinuous time segments. Further, the controller is configured to provide an output based on the discontinuous recording. In practice, the controller in this arrangement can be provided in the hearing prosthesis. Alternatively, the controller can be provided in a device or system that is separate from the hearing prosthesis and that is in communication with the hearing prosthesis. For instance, the controller can be provided in a cell phone or other device carried by a recipient of a hearing prosthesis.

In addition, in still another respect, disclosed is a hearing prosthesis that includes a microphone, a stimulator that is configured to stimulate a physiological system of a recipient, and a controller. In practice, the controller is configured to receive, using the microphone, audio input representing an audio environment. Further, the controller is configured to discontinuously record the received audio input, with the discontinuous recording including recording discontinuous time segments of the received audio input without recording portions of the audio input between the discontinuous time segments. Yet further, the controller is configured to provide an output based on the discontinuous recording.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

DETAILED DESCRIPTION

The present disclosure will focus on application in the context of hearing prosthesis or hearing prosthesis system. It will be understood, however, that principles of the disclosure can be applied as well in numerous other contexts, such as with respect to numerous other types of devices or systems that receive audio input. Further, even within the context of hearing prostheses, it will be understood that numerous variations from the specifics described will be possible. For instance, particular features could be rearranged, re-ordered, added, omitted, duplicated, or otherwise modified.

Devices as described herein can operate to receive audio input from an audio environment and to perform operations based on such received audio input. An audio environment at a particular location includes any sounds that are present at the particular location. Such an audio environment could include sounds generated by a variety of sources that are proximate to the particular location or that are sufficiently loud that sound produced by the source is able to propagate to the particular location. Sound sources could include people, animals, machinery or other artificial devices, or other objects. Further, sound sources could include motion or other processes of the air at a particular location. For instance, an audio environment can include wind noise produced at a particular location (e.g., the location of a microphone) by the motion of air around objects at the particular location. An audio environment could include sounds provided by other sources as well.

Figure 1:
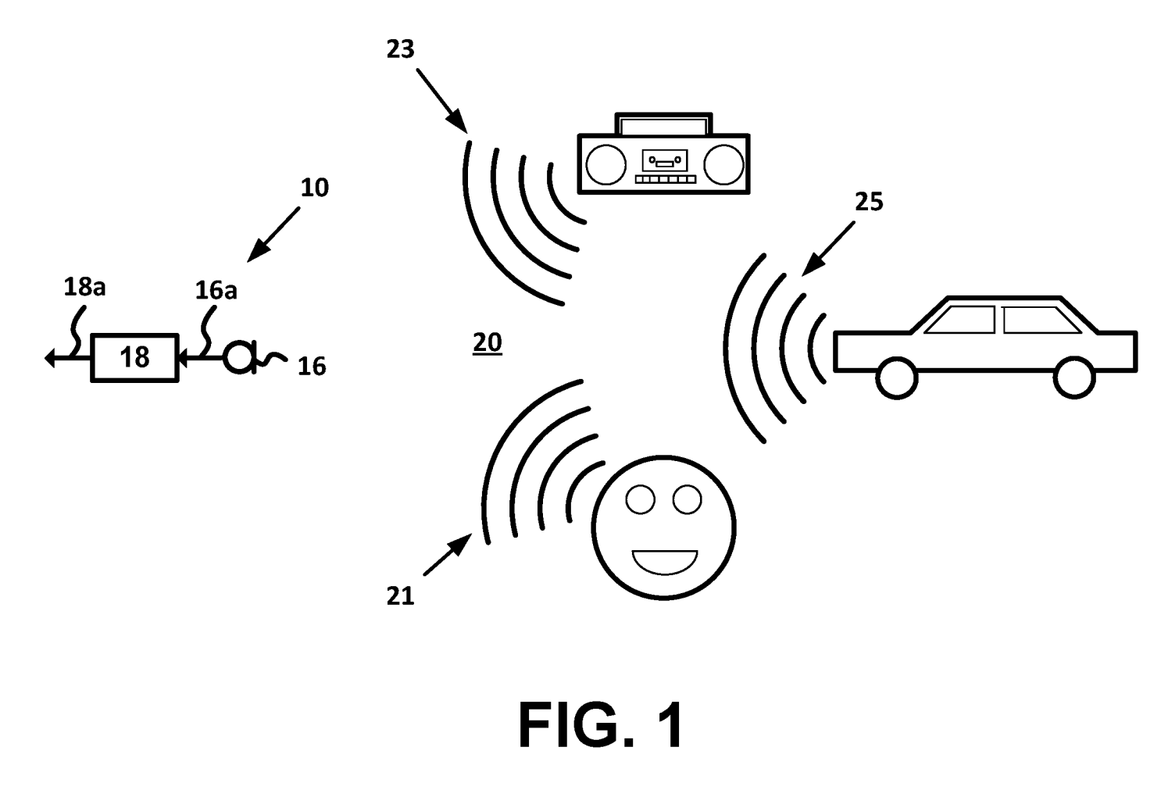
FIG. 1 shows a device that is configured to receive audio input from an example audio environment.

Referring to the drawings, FIG. 1 is an illustration of a hearing prosthesis 10 that includes a microphone 16. The microphone 16 is configured to receive audio input from an audio environment 20 of the hearing prosthesis 10. By way of example, the audio environment 20 depicted in FIG. 1 includes speech 21 produced by a person near the device, music 23 produced by a personal stereo, and mechanical noise 25 produced by an automobile. Further, hearing prosthesis 10 includes a controller 18 that is configured to receive audio input 16a from the microphone 16, to discontinuously record the received audio input 16a, and to provide an output 18a based on the discontinuously recorded audio input. The controller 18 is also configured to present, based on the received audio input 16a from the microphone 16, stimulation to a recipient of the hearing prosthesis 10 such that the recipient can receive percepts related to the audio environment 20 (e.g., percepts that can facilitate the recipient perceiving information content of the speech 21).

Figure 2A:
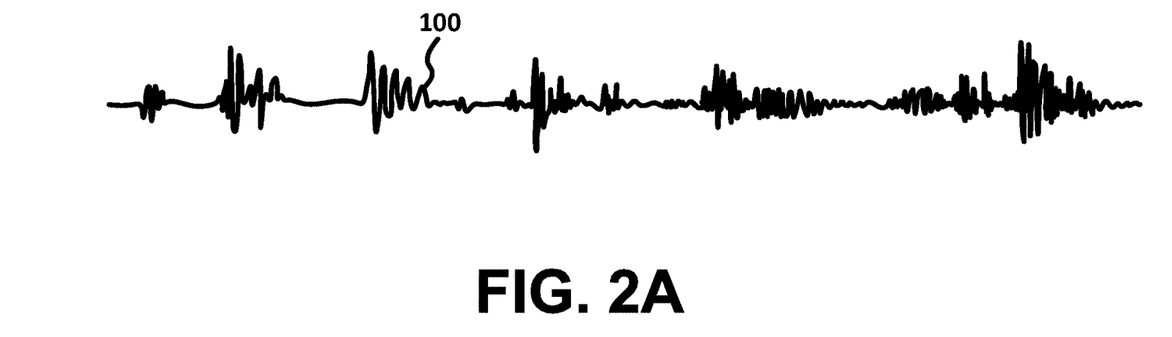
FIG. 2A is a graphical illustration of an example audio input.

Audio input (e.g., 16a) that is received from an audio environment can include speech, noise, music, or other sounds related to the contents of the audio environment. FIG. 2A is a graphical depiction of representative audio input 100. Such audio input 100 can be received by a hearing prosthesis, by a device operating in conjunction with a hearing prosthesis, or by some other device. The audio input 100 could represent music, speech of a recipient, speech of others, speech produced by a speaker, background noise, or other sounds present in an audio environment. As shown in FIG. 2A, representative audio input 100 includes pulses of sound separated by periods of relative quiet. In examples wherein the audio input 100 has been received from an audio environment that includes speech, the illustrated pulses of sound could correspond to words of speech produced by the mouth of a person or produced by a speaker or other device configured to produce speech sounds.

As noted above, it can be useful to provide a recording of the audio input 100 in a manner that facilitates evaluation of acoustic content (e.g., a noise level or a frequency content) of the audio environment while masking speech content from the audio environment. For instance, recorded audio can be output as sound to allow an audiologist or other person to experience or evaluate the audio environment represented by the audio input. Such an evaluation can include changing or setting one or more parameters (e.g., filter bank coefficients of an audio processor) of a hearing prosthesis to improve the intelligibility of speech or other audio precepts presented, by the hearing prosthesis, to a recipient of the hearing prosthesis. In another example, such recorded audio input that is output as sound could be used by a recipient of a hearing prosthesis to remember a situation when the recipient experienced difficulty using their hearing prosthesis or to recall information about some other event of interest represented by the recorded audio input.

Such masking can help to preserve the privacy of individuals who produced the speech content. This could be accomplished by recording discontinuous time segments of the audio input 100 without recording the audio input 100 between such discontinuous time segments. Omission of the audio input 100 between the discontinuous time segments can help to reduce the intelligibility of any speech that may be present in the audio input 100. The durations of such discontinuous time segments, the intervals between such discontinuous time segments, the timing of the discontinuous time segments, or other properties of the recorded discontinuous time segments can be defined in a variety of ways to mask speech or other private content that may be present in the audio input 100. Further, such discontinuous recording of audio input can be performed by a device while using very little additional energy (e.g., from a battery of the device), owing to the relative simplicity of discontinuous recording relative to other methods of masking speech or other private content in audio input (e.g., by performing time- or frequency-domain filtering of the audio input or by detecting the presence, timing, or other information about speech that may be present in the audio input and selectively removing or distorting the speech when present).

The omission of phonemes, words, or other speech content that is present between such recorded discontinuous time segments, for instance, can cause such a reduction in intelligibility. If the pulses of sound present in the representative audio input 100 correspond to individual words or phonemes, recording only the audio input 100 during discontinuous time segments that are sufficiently short and that are spaced sufficiently far apart in time produces a recording of only portions of the words or phonemes. Further, as the timing of such time segments can be substantially independent of the timing of the speech content (e.g., the timing of words of the speech content), words, phonemes, or portions thereof that are recorded may be insufficient to determine sentences, names, or other private information that may be present in the audio input 100.

As noted above, the intelligibility of speech in discontinuously recorded time segments of an audio input (e.g., audio input 100) can be reduced by increasing the duration of intervals between such discontinuous time segments. This reduced intelligibility could be related to an increased amount of the audio input being omitted from the discontinuous recording, a decreased likelihood of recorded phonemes or words being related to the same sentence or concept, or other factors. Thus, to help preserve the privacy of people whose speech is present in the audio input, the duration of intervals between discontinuously recorded time segments of the audio input can be made greater than some specified minimum duration. For example, the discontinuous time segments can be separated in time by intervals that are more than approximately 800 milliseconds.

Intelligibility of speech in an audio input (e.g., 100) can also be reduced by decreasing the duration of the discontinuous time segments. This reduced intelligibility could be related to a decreased likelihood of a complete word, phoneme, or other intelligible unit of speech being present in the audio input during any one of the recorded discontinuous time segments. Thus, to help preserve the privacy of people whose speech is present in the audio input, the duration of the discontinuous time segments can be less than some specified minimum duration. Such a specified minimum duration can be made less than an expected length of a word of speech, that is, less than approximately 400 milliseconds. For example, the discontinuous time segments can have durations that are less than approximately 200 milliseconds.

A device can discontinuously record time segments of an audio input that are regularly spaced in time (e.g., the device could record discontinuous time segments of an audio input at a set rate), that are irregularly spaced in time (e.g., that have inter-segment intervals that are randomly generated), or that are timed in some other way. Further, a device can record discontinuous time segments of the audio input that have the same duration, or that vary.

Figure 2B:
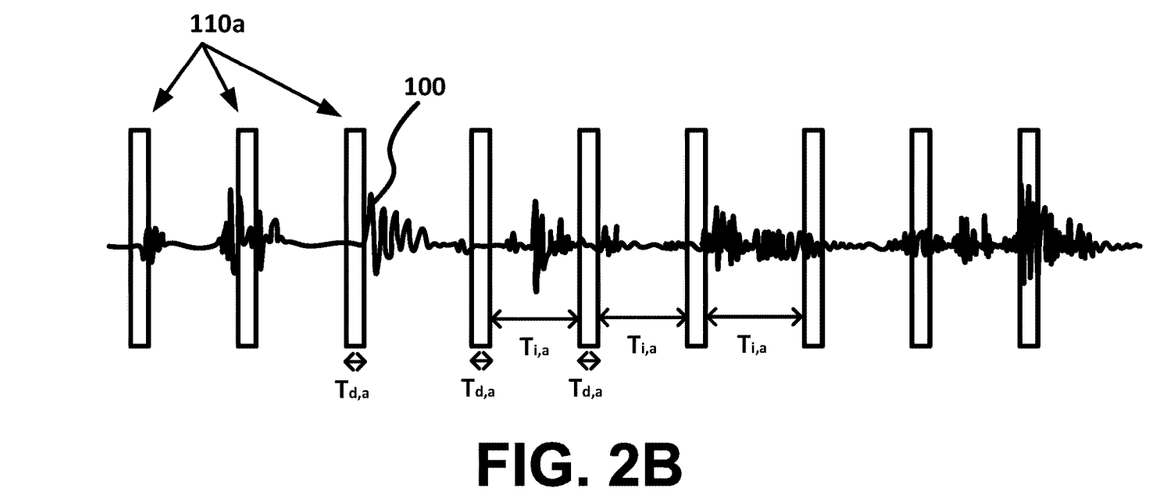
FIG. 2B is an example timing diagram of discontinuously recorded time segments of the audio input of FIG. 2A.

To illustrate the discontinuous recording of audio input by way of an example, FIG. 2B shows, overlaid on the audio input 100, first example discontinuous segments of time 110a. The audio input 100 can be discontinuously recorded by recording portions of the audio input 100 that are received during the time segments 110a and not recording the intervening portions. In this example, the discontinuous time segments 110a are separated by intervals of time that all have the same duration, $T_{i,a}$, and thus the time segments 110a are regularly spaced in time. As noted above, the duration of the intervals of time between the segments 110a, $T_{i,a}$, can be greater than a minimum value (e.g., 800 milliseconds) to reduce the intelligibility of speech recorded in the discontinuous time segments. Further, the duration of the time segments 110a themselves, $T_{d,a}$, can be less than a minimum value (e.g., 200 milliseconds) to further reduce the intelligibility of speech recorded in the discontinuous time segments, as well.

In a further aspect, a device as described herein can receive audio input, which can then be discontinuously recorded by the device, in a variety of ways. A device can receive audio input directly from an audio environment, e.g., using a microphone or other sound detecting means of the device. Additionally or alternatively, a first device can provide audio input to a second device, e.g., via a wired or wireless communications link. The second device can then discontinuously record the provided audio input. For example, a hearing prosthesis (e.g., a hearing aid, a cochlear implant system, or a bone conduction implant system) can detect, using one or more microphones of the hearing prosthesis, audio input from an audio environment. The hearing prosthesis can then provide the detected audio input to another device. A controller or other elements of the other device can then discontinuously record the received audio input. The other device can be another hearing prosthesis, a logging device, a cell phone, or some other device configured to receive and to discontinuously record audio input provided by the hearing prosthesis.

Further, a device or other system configured to discontinuously record audio input can provide output based on the discontinuous recording. This can include a device providing the recorded discontinuous portions of the audio input to some other device or system. Additionally or alternatively, a device can apply an audio analysis algorithm to determine some information (e.g., a power spectrum, a noise level, or a sound intensity), based on the recorded discontinuous portions of the audio input, to characterize the discontinuously recorded time segments of the audio input. The device can then provide the determined information in addition to or instead of providing the recorded discontinuous time segments of the audio input.

A device can provide such output continuously, at discrete points in time, or according to some other consideration. For instance, a device can provide output as the device discontinuously records time segments of an audio input and/or as the device determines information based on the discontinuous time segments. Additionally or alternatively, a device can maintain recorded discontinuous time segments of an audio input, or information determined therefrom, in a data storage of the device. The device can then output such stored information, e.g., in response to a request for such output. Further, a device can provide such stored discontinuous time segments of an audio input out-of-order to further reduce the intelligibility of any speech that is present in the recorded audio input.

A controller or other device configured to discontinuously record audio input can provide outputs based on the discontinuous recording in a variety of ways. A device can provide the output to a person as sound, e.g., using a speaker. The device can provide this sound output in response to receiving a request from the person, e.g., via a user interface of the device. Additionally or alternatively, a component of a device can provide the output to another component of the device or to a different device. For instance, a controller of a device can discontinuously record an audio input and provide output based on the recording to a data storage of the device. Alternatively, a first device can provide output to another device or system. In an example, a device can provide the output to a cloud service or to some other service on the Internet. In another example, a hearing prosthesis can provide an output to another device configured to receive such output. For instance, the hearing prosthesis can provide the output to a dedicated recording device carried by a recipient of the hearing prosthesis, or a cell phone configured to record and/or upload to a server the outputs provided by the hearing prosthesis.

A device configured to discontinuously record audio input can also detect trigger events that are associated with the audio input. Detected trigger events could provide context for discontinuously recorded time segments of the audio input, e.g., to help characterize an audio environment, to help in using the recorded time segments to control a setting of a hearing prosthesis, or to indicate which time segments of the audio input were received proximate to an event of interest. A device can record the occurrence of such trigger events and/or can control the discontinuous recording of audio input based on the occurrence of such trigger events. For example, a device can begin discontinuously recording the audio input in response to detecting the occurrence of such an event. Further, a device can determine data about a trigger event (e.g., a timing of the trigger event, an identity of the trigger event, or the content of a command or other input constituting the trigger event that is received from a user) and can output the data to another system, e.g., to a system that the device is providing with outputs based on recorded discontinuous segments of the audio input.

A device can detect a variety of different trigger events that are associated with a discontinuously recorded audio input. For example, a device can detect a trigger event based on a user input to the device. The user input can include an indication that audio input should be recorded (such as an express user request to begin recording), a command to set an operational mode of a hearing prosthesis (e.g., to change a volume level, to change a filter bank setting, or to change a predicted audio environment), or some other input to the device. In a further example, a device can detect a trigger event based on a change in an operational mode of the device. For instance, the device can be a hearing prosthesis and the detected trigger event can include the hearing prosthesis changing filter bank coefficients or changing some other parameters used to process the audio input to stimulate a physiological system of a recipient, perhaps in the course of normal operation of the prosthesis and/or in response to user input.

Yet further, a device can detect a trigger event by detecting a change in the audio environment of the device. This can include the device determining that an acoustic content of the audio environment (e.g., a noise level, a power spectrum, or a power within one or more bands of frequencies) matches a particular acoustic template. Such acoustic templates can be specified to represent different types of audio environment, e.g., to represent audio environments that contain speech, speech and noise, noise, music, or other sounds. A device could detect the occurrence of other types of trigger events as well.

As noted above, a device can detect the occurrence of a trigger event to provide context for the discontinuously recorded time segments of the audio input. This can include identifying one or more particular time segments that are proximate in time to the detected occurrence of a trigger event. For instance, the device can identify a particular time segment that immediately precedes the occurrence of the trigger event, a particular time segment that is closest in time to the occurrence of the trigger event, or a set of time segments that are within a specified period of time relative to the occurrence of the trigger event.

Figure 2C:
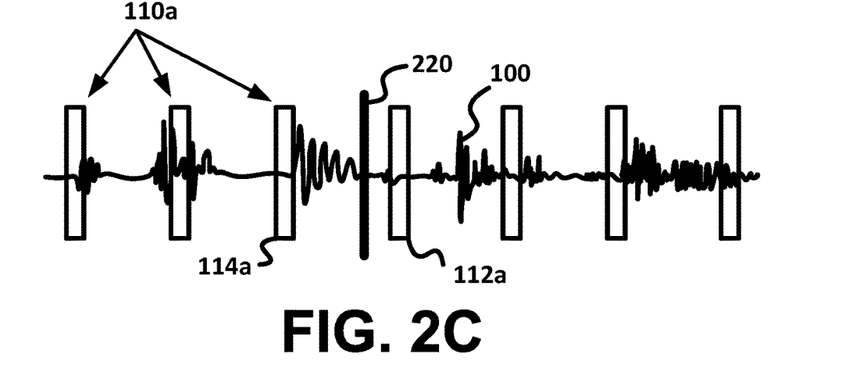
FIGS. 2C and 2D are example timing diagrams of discontinuously recorded time segments of the audio input of FIG. 2A and an event providing context for the discontinuously recorded time segments.

To illustrate this, FIG. 2C shows the timing of an example trigger event 220 relative to the first example discontinuous time segments 110*a*. The trigger event 220 and the time segments 110*a* are overlaid on the audio input 100. A device can determine the timing of the trigger event 220 relative to the time segments 110*a* by identifying one or more particular time segments that are proximate in time to the occurrence of the trigger event 220, e.g., a time segment that is closest in time to the occurrence of the trigger event 220 (e.g., time segment 112*a*) or a time segment that is immediately preceding the occurrence of the trigger event 220 (e.g., time segment 114*a*). The device can then provide an output based on such identified time segment(s).

Figure 2D:
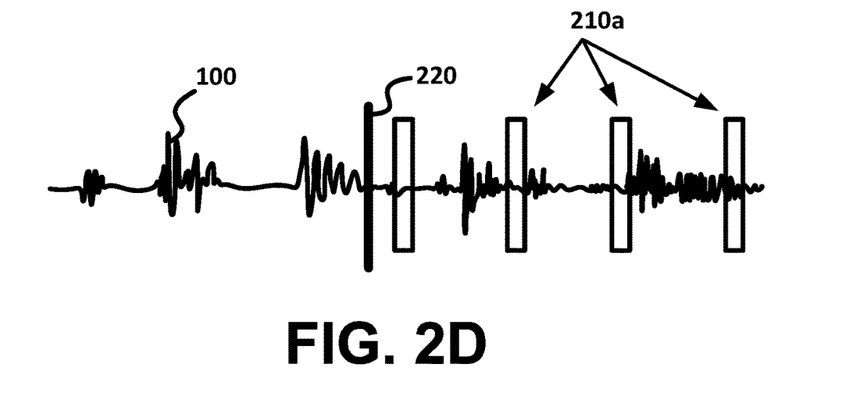

As noted above, a device can detect the occurrence of a trigger event that is associated with discontinuously recorded audio input and then record some information about the detected trigger event. Additionally or alternatively, the device can set or change a timing, duration, or other properties of the discontinuous recording of the audio input in response to detecting the occurrence of the trigger event. For instance, the device can begin to discontinuously record an audio input in response to detecting a trigger event. This could include the device recording a discrete number of discontinuous time segments of an audio input, or the device beginning to record discontinuous segments of the audio input indefinitely. As an illustrative example, FIG. 2D shows the timing of the example trigger event 220 overlaid on the audio input 100. In response to detecting the occurrence of the trigger event 220, a device can begin recording discontinuous time segments 210*a* of the audio input 100.

As illustrated in FIG. 2D, a device can, responsive to detecting the occurrence of a trigger event, record discontinuous time segments of audio input that are received after the occurrence of the trigger event. However, it can be beneficial to record time segments of audio input that are received before the occurrence of a detected trigger event. For example, a device can detect a user-input to change an operational mode of a hearing prosthesis. In such an example, it could be beneficial to characterize whatever changes may have occurred in the audio environment, before receipt of the user-input, to prompt the user to change the operational mode.

Figure 2E:
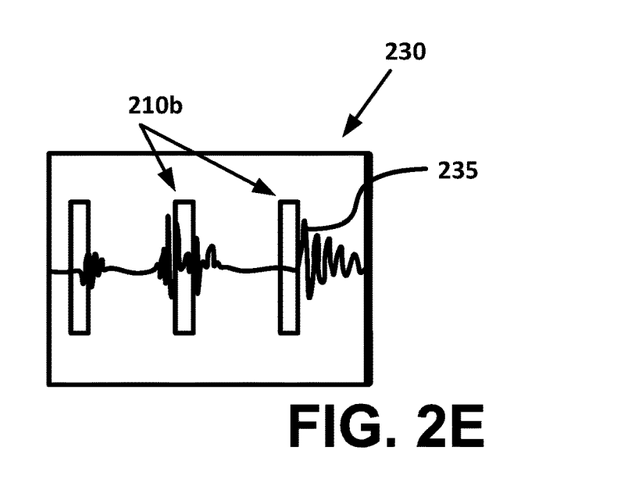
FIG. 2E is an example timing diagram of discontinuously recorded time segments of the audio signal of FIG. 2A, where the time segments are recorded from a buffer containing the audio signal.

Accordingly, a device can discontinuously record time segments of an audio input that are received before and/or after the occurrence of a trigger event in a variety of ways. For instance, the device can maintain a buffer of the audio input in a data storage of the device. The device can record the audio input in the buffer and subsequently discard the recorded audio input unless a trigger event is detected. If the device detects a trigger event, the device can record, from the buffer, discontinuous time segments of previously received audio input. Other contents of the buffer, containing portions of the audio input between the discontinuous time segments that were recorded from the buffer, can be discarded. As an illustrative example, FIG. 2E shows the contents of a buffer 230 of a device at the time when the device detects the trigger event 220. As shown, the device can use the buffer 230 to maintain a record of recently received audio input 235. Responsive to detecting the trigger event 220, the device can record, from the buffer 230, discontinuous time segments 210*b* of the audio input 235. Thus, the recorded discontinuous time segments 210*b* contain audio input received prior to the occurrence of the trigger event 220. A device can operate in other ways to record discontinuous time segments of audio input that are received before detection of a trigger event, as well.

A variety of systems or devices can perform the described methods of discontinuously recording an audio input. Such devices can perform additional actions, as well, e.g., to detect the audio input using a microphone, to present stimulus to a physiological system of a recipient based on the audio input, or to receive user inputs. Conversely, a device that is not configured to discontinuously record audio input can be configured to facilitate such recording by another device, e.g., by providing an audio input to the other device. For instance, a first device can discontinuously record audio input provided by a second device (e.g., an element of a cochlear prosthesis or other hearing prosthesis that is configured to detect the audio input from an audio environment). In another example, a first device that is discontinuously recording an audio input can receive, from a second device (e.g., a control pendant, a cell phone running a prosthesis control app), inputs from a user that are related to the audio input.

Figure 3:
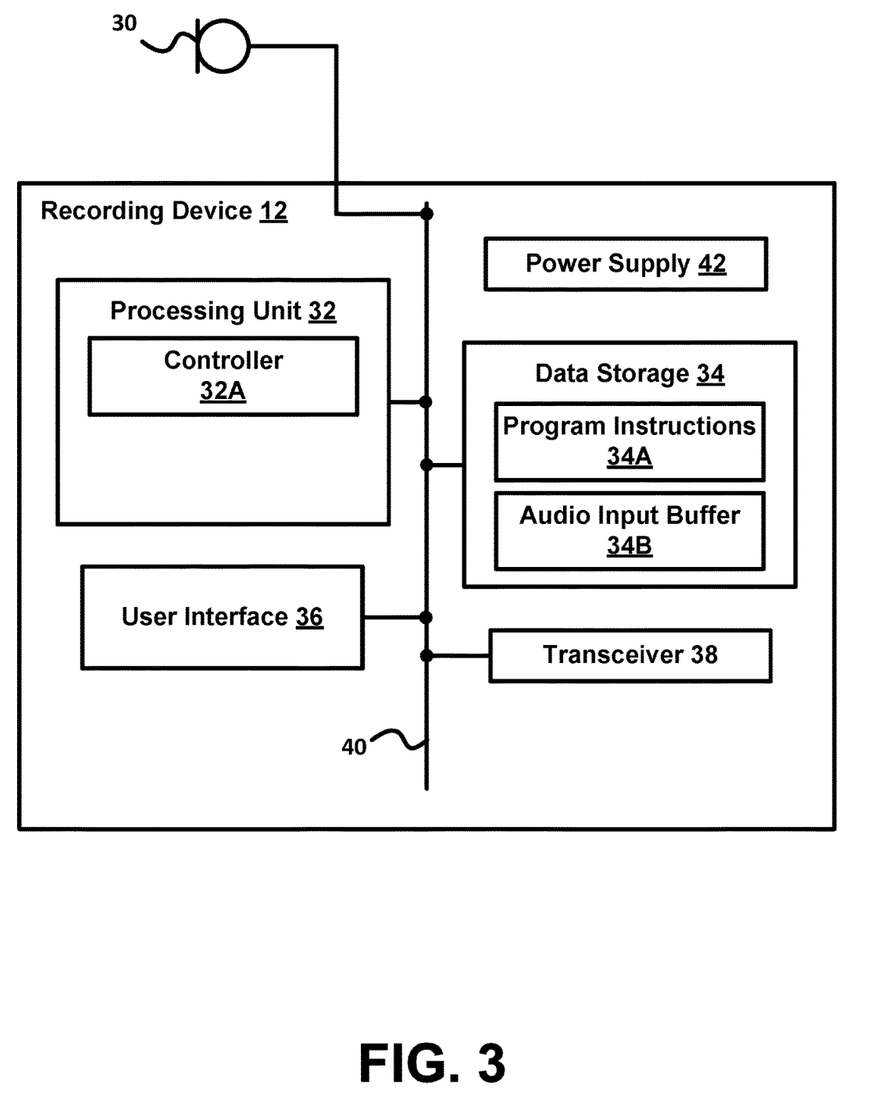
FIG. 3 is a simplified block diagram depicting components of an example external unit of a hearing device.

Turning now to FIG. 3, an example recording device 12 is illustrated that can discontinuously record an audio input. The recording device 12 includes a microphone (or other audio transducers) 30, a processing unit 32, data storage 34, an output component 36, and a transceiver 38, which are communicatively linked together by a system bus, network, or other connection mechanism 40. The recording device 12 also includes a rechargeable battery 42 that provides power to the components of the recording device 12, a user interface 36 for receiving inputs from a user and/or for providing outputs to the user, and a transceiver 38 to facilitate communications with other devices or systems.

The recording device 12 can be implemented in a variety of ways. In some examples, the recording device 12 can be a cell phone or other general purpose device that includes applications or programs that can be executed (e.g., by the processing unit 32) to discontinuously record an audio input. Alternatively, the recording device 12 can be part of a hearing prosthesis that is configured to receive audio input and to stimulate a physiological system of a recipient to provide perceptions related to the audio input. For example, the recording device 12 can be an external unit of a cochlear implant system, and the transceiver 38 can be electrically connected to a transducer, such as an inductive coil, that is configured to provide data and/or power to an implanted stimulation unit of the cochlear implant system.

In the arrangement as shown, the microphone 30 may be positioned to receive sounds, such as audio coming from an audio environment, and to provide a corresponding signal (e.g., electrical or optical, possibly sampled) to the processing unit 32. For instance, the microphone 30 may be positioned on an exposed surface of the housing of the recording device 12. Further, the microphone 30 may comprise additional microphones and/or other audio transducers, which can also be positioned on an exposed surface of the housing of the recording device 12.

The processing unit 32 may then comprise one or more digital signal processors (e.g., application-specific integrated circuits, programmable logic devices, etc.), as well as analog-to-digital converters. As shown, at least one such processor functions as a controller 32A, to discontinuously record audio input as discussed above. Such audio input can be detected using the microphone 30 of the recording device 12. Additionally or alternatively, controller 32A can operate to discontinuously record audio input that is received by some other means. For example, audio input can be received from another device, e.g., by receiving a transmission, using the transceiver, from the other device.

The data storage 34 may then comprise one or more volatile and/or non-volatile storage components, such as magnetic, optical, or flash storage, and may be integrated in whole or in part with processing unit 32. As shown, the data storage 34 may hold program instructions 34A executable by the processing unit 32 to carry out various functions described herein. The data storage 34 may further hold an audio input buffer 34B that can be used, by the processing unit 32, to temporarily maintain received audio input in the data storage 34.

By way of example, the program instructions 34A may be executable by the processing unit 32 to facilitate receiving audio inputs via the microphone 30, to record discontinuous time segments of such received audio input, and to provide outputs based on such discontinuously recorded time segments. For instance, the program instructions 34A may include instructions for selecting discontinuous time segments of the audio input to record (e.g., according to a specified rate of the time segments, a specified duration of the time segments, a specified interval between the time segments, or a specified range or probability distribution of intervals between the time segments). The program instructions 34A may further include instructions for determining some information about the recorded time segments, e.g., for determining a noise level, a noise spectrum, an acoustical content, or some other information about the recorded time segments.

Additionally, the instructions may cause the processing unit 32 to detect the occurrence of a trigger event and to perform some operations responsive to detecting the trigger event. Such operations can include recording information, including a timing, about the trigger event. In some examples, the instructions may cause the processing unit 32 to begin discontinuously recording audio input in response to detection of the trigger event. Detecting occurrence of a trigger event can include determining some information about a received audio input, e.g., determining that an acoustical content of the audio input matches a particular acoustical template. Detecting occurrence of a trigger event can include operating the user interface 36 to receive an input and determining that the received input satisfies some criterion. For example, detecting occurrence of a trigger event can include determining that a received user input includes a command to change an operational mode of the recording device 12, or to change an operational mode of some other device. Detecting occurrence of a trigger event can include performing some other operations.

The instructions may additionally cause the processing unit 32 to provide an output related to discontinuously recorded time segments of the audio input. The provided output can include the recorded audio input and/or information determined by the processing unit 32 therefrom (e.g., acoustical content, noise levels, or power spectra). The output can be provided, as sound generated by a speaker (e.g., a speaker of the user interface 36), to a person. The output can be provided to another device, as a wired or wireless transmission, via the transceiver 38. The output can be provided from the processing unit 32 to another element of the recording device 12, e.g., to the data storage 34. Such recorded discontinuous segments of audio input, once stored in the data storage 34, can later be provided from the recording device 12 to another system or device or to a person, as sound.

Hearing prostheses can include, or be part of, devices or systems that are configured to discontinuously record an audio input. Hearing prostheses are devices or systems configured to provide stimulation to a physiological system of a recipient such that the recipient can perceive a sound related to the provided stimulation. A hearing prosthesis can provide such stimuli based on audio input detected by the hearing prosthesis (e.g., using a microphone of the hearing prosthesis) or based on audio input received from some other source (e.g., from an external microphone, a media player, a cell phone, or some other device or system that is in communication with the hearing prosthesis).

Figure 4:
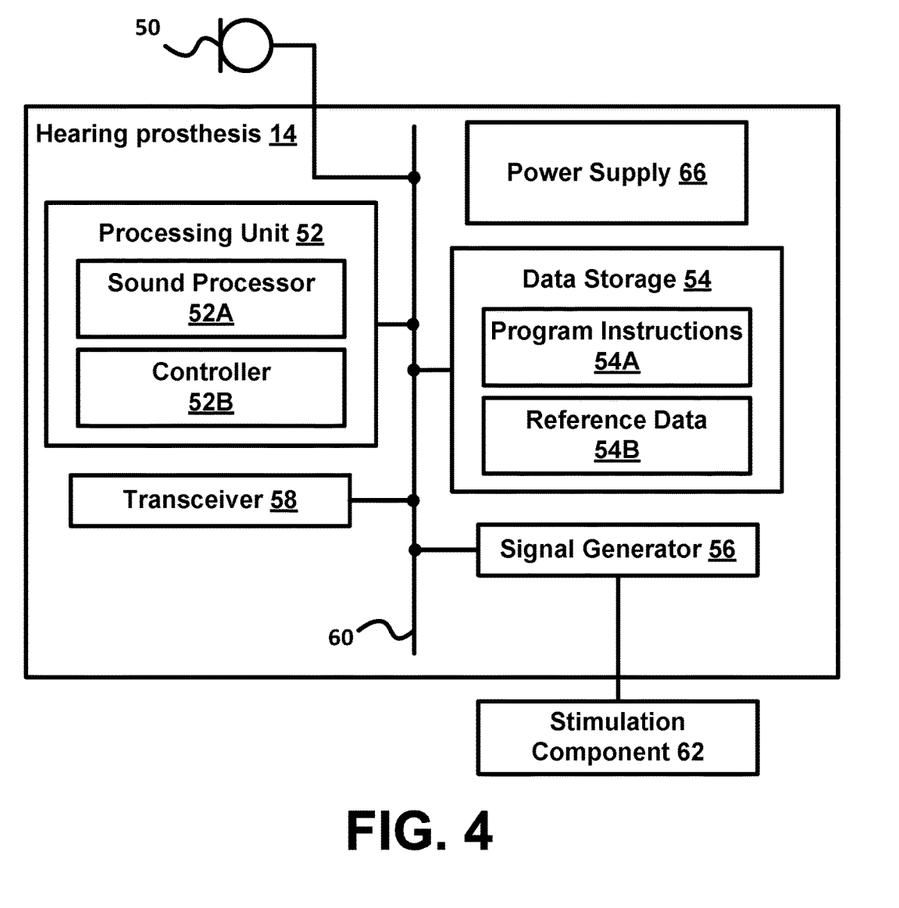
FIG. 4 is a simplified block diagram depicting components of an example stimulation unit of a hearing device.

As an illustrative example of a hearing prosthesis that can operate to discontinuously record an audio input, FIG. 4 shows a schematic of a hearing prosthesis 14. The hearing prosthesis 14 includes a microphone (or another audio transducer) 50, a processing unit 52, data storage 54, a signal generator 56, and a transceiver 58, which are communicatively linked together by a system bus, network, or other connection mechanism 60. The hearing prosthesis 14 may further include a power supply 66, such as a rechargeable battery, that is configured to provide an alternate power source for the components of the hearing prosthesis 14 when power is not supplied by some external system.

In an example arrangement, each of these components, with the possible exception of the microphone 50 and the stimulator 62, are included in a single housing implanted in the recipient. Alternatively, the power supply 66 may be included in a separate housing implanted in the recipient to facilitate replacement. In a particular arrangement, elements of the hearing prosthesis 14 can be separated into an external unit (that includes, e.g., a battery of the power supply 66, the microphone 50, or some other elements) that is configured to be removably mounted on the outside of a recipient's body (e.g., proximate an ear of the recipient) and an implanted unit (that includes, e.g., the signal generator 56 and the stimulation component 62). The external unit and implanted unit can each include respective transducers, such as inductive coils, to facilitate communications and/or power transfer between the external unit and implanted unit. Other arrangements are possible as well.

In the arrangement as shown, the stimulation component 62 can include a variety of means configured to stimulate a physiological system of the recipient. The stimulation component 62 can include electromechanical components configured to mechanically stimulate the eardrum, ossicles, cranial bones, or other elements of the recipient's body. Additionally or alternatively, the stimulation component 62 can include electrodes or other means configured to electrically stimulate the cochlea, hair cells, nerves, brainstem, or other elements of the recipient's body.

The processing unit 52 may be similar to the processing unit 32 described with respect to FIG. 3. As shown, a sound processor 52A may process received audio input from the microphone 50, or from some other source, to enable generation of corresponding stimuli when the stimulation component 62 operates to stimulate the recipient. In processing such sounds, the sound processor 52A may be configured to remove internal sounds (e.g., sounds from the recipient's organs) prior to generating the stimuli. Such stimulation provided to a recipient can be determined based on the received audio input, rather than based on a discontinuously recorded version of the received audio input, such that the recipient can, based on the provided stimulation, interpret the information content of speech that may be present in the received audio. Another controller 52B of the processing unit 52 can be configured, as described above for controller 32A, to record discontinuous time segments of a received audio input or to perform other functions related to such discontinuous recording. Alternatively, all processing functions, including functions for discontinuously recording audio input, can be carried out by the sound processor 32A itself.

The data storage 54 may, like the data storage 34, then comprise one or more volatile and/or non-volatile storage components, such as magnetic, optical, or flash storage, and may be integrated in whole or in part with processing unit 52. As shown, the data storage 54 may hold program instructions 54A executable by the processing unit 52 to carry out various hearing prosthesis functions described herein, as well as reference data 54B that the processing unit 52 may reference as a basis to carry out various such functions.

The signal generator 56 may include a pulse generator, a controlled-current amplifier, a multiplexer, and other hardware suitable for generating stimuli. Upon receipt of electrical signals from the processing unit 52, the signal generator 56 may responsively cause the stimulation component 62 to deliver one or more stimuli to a body part of the recipient, thereby causing the recipient to perceive at least a portion of a sound. By way of example, the stimulation component 62 may be an electrode array inserted in cochlea of the recipient, in which case the stimuli generated by the signal generator 56 are electrical stimuli. As another example, the stimulation component 62 can be a bone conduction device, and the signal generator 56 may generate electromechanical stimuli. In yet another example, the stimulation component 62 may be a transducer inserted or implanted in the recipient's middle ear, in which case the signal generator 56 generates acoustic or electroacoustic stimuli. Other examples are possible as well.

Note that, while the hearing prosthesis 14 is configured to discontinuously record an audio input, the hearing prosthesis can additionally or alternatively be configured to provide such audio input to an external system (e.g., via the transceiver 58). Such an external system can then discontinuously record the audio input received form the hearing prosthesis 14.

Figure 5:
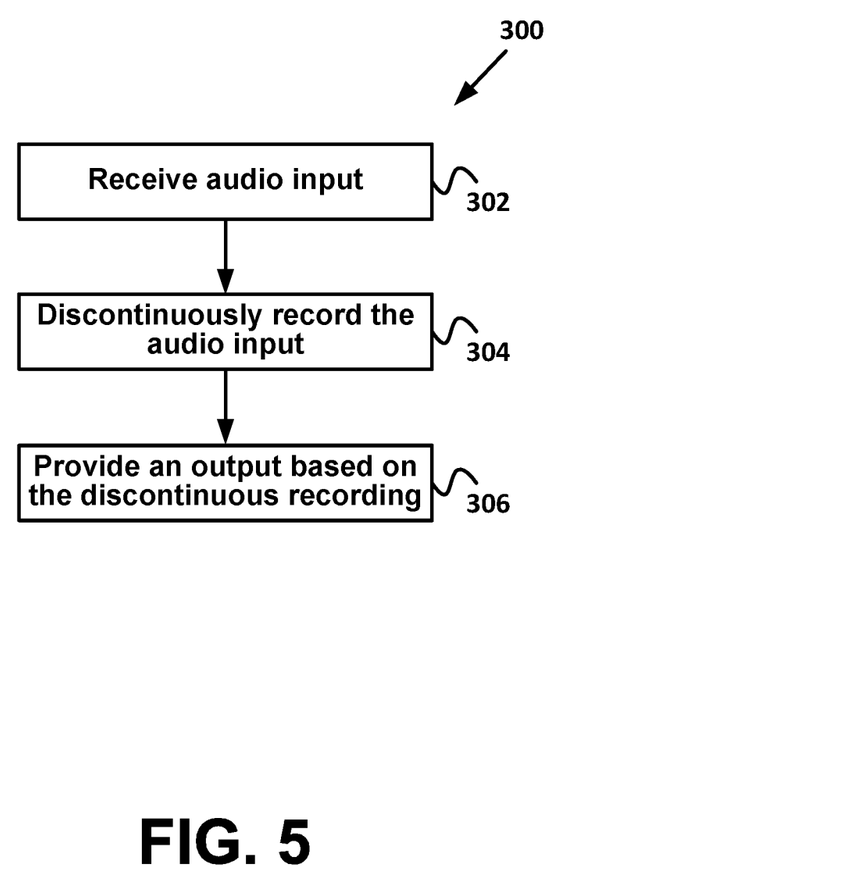
FIG. 5 is a flow chart depicting functions that can be carried out in accordance with the present disclosure.

Finally, a flow chart is shown in FIG. 5 to illustrate functions of a method 300. The method 300 includes discontinuously recording received audio input. The method 300 can be performed by hearing prostheses or other devices or systems as described elsewhere herein, or by further devices or systems as will be known to one of skill in the art.

The method 300 begins at block 302 with an audio input being received. At block 304, the received audio input is discontinuously recorded. Such discontinuous recording can include recording discontinuous time segments of the received audio input without recording portions of the audio input between the discontinuous time segments. An output is then provided, at block 306, that is based on the discontinuous recording of the audio input.

Receiving an audio input 302 can include operating a microphone, or other means for detecting sound, to receive the audio input from an audio environment. Additionally or alternatively, audio input can be received via a wired or wireless communication link, or from a data storage of a device that is configured to perform the method 300. For example, the audio input can be detected by a hearing prosthesis and provided, via a wireless communications link, to a device configured to discontinuously record the provided audio input.

Further, discontinuously recording the audio input 304 includes recording a plurality of time segments of the audio input. An interval between one or more of the time segments, a rate of occurrence of the time segments, a duration of one or more of the time segments, or some other properties of the timing of the recorded discontinuous time segments of the audio input can be specified to decrease the intelligibility of any speech that may be present in the discontinuously recorded audio input. Accordingly, each recorded discontinuous time segment can be separated in time from other recorded discontinuous time segments by more than some specified minimum, e.g., more than approximately 800 milliseconds. The intelligibility of such speech can also be decreased by setting the duration of the discontinuous time segments below some specified minimum, e.g., less than approximately 200 milliseconds.

Additional information, such as information related to events associated with the audio input, can be recorded. Information about such trigger events can be recorded and output along with outputs based on the discontinuously recorded audio input. Such trigger events can include the received audio input matching some criterion, the receipt of a user input, or some other trigger events. A timing or other information about the occurrence of such trigger events can be recorded, and subsequently output. Additionally or alternatively, the discontinuous recording 305 can begin, or a timing or other properties of recorded discontinuous time segments can be changed, in response to detection of a trigger event.

Finally, the method 300 includes providing an output based on the discontinuous recording. The provided output can include the recorded time segments of the audio input and/or some other information determined therefrom. For example, the output can include a power spectrum, a noise level, an acoustic content, or some other information determined based on the recorded discontinuous time segments. The output can be provided based on each recorded discontinuous time segments as such time segments are recorded, the output can be provided based on a number of recorded time periods at a time, or the output can be provided according to some other scheme. The output can be provided to a person, e.g., as sound, or to a device or system that is separate from a device that is performing the method 300, e.g., as a wired or wireless transmission. Additionally or alternatively, a controller that is discontinuously recording an audio input according to the method 300 can provide the output to another element (e.g., a data storage) of a device that includes the controller.

In practice, elements of the method 300 can be performed at the same time. That is, a device configured to perform the method 300 can operate, on an ongoing basis, to receive audio input from an environment 302, to record discontinuous time segments of the received audio input 304, and to provide output based on the recorded discontinuous time segments 306. Alternatively, one or more of the elements of the method 300 can be discretely performed one or more times. For instance, a device can operate on an ongoing basis to receive an audio input and to discontinuously record the audio input. The discontinuously recorded audio input, or information determined therefrom, can be maintained in a data storage. The information maintained in the data storage can then, in response to a request for output or based on some other consideration or factor, be output. In another example, a device can operate on an ongoing basis to receive audio input and to detect a trigger event. In response to detecting an occurrence of the trigger event, the device can begin discontinuously recording the audio input and/or performing some other functions.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. A method comprising:
   receiving audio input, wherein the received audio input represents an audio environment and includes speech;
   discontinuously recording the received audio input, wherein the discontinuous recording comprises recording discontinuous time segments of the received audio input without recording portions of the audio input between the discontinuous time segments, wherein one or more of the discontinuous time segments have time durations that are less than an average duration of words of speech, and whereby omitting from the discontinuous recording the portions of the audio input between the discontinuous time segments reduces intelligibility of the speech in the audio input; and
   providing an output based on the discontinuous recording of the received audio input.

2. The method of claim 1, wherein receiving audio input comprises receiving audio input into a hearing prosthesis that is operable to stimulate a physiological system of a recipient in accordance with the received audio input, wherein the audio environment is an audio environment of the recipient.

3. The method of claim 2, further comprising:
   transmitting, by the hearing prosthesis, the received audio input to an external device, wherein the discontinuous recording of the received audio input is performed by the external device.

4. The method of claim 1, further comprising:
   detecting occurrence of a trigger event, wherein discontinuously recording the received audio input is performed responsive to detecting occurrence of the trigger event.

5. The method of claim 4, further comprising:
   receiving a user input, wherein detecting occurrence of the trigger event comprises determining that the received user input includes a command to set an operational mode of a hearing prosthesis.

6. The method of claim 5, wherein receiving the user input comprises receiving, into the hearing prosthesis from an external device, an indication related to the user input.

7. The method of claim 4, further comprising:
   determining an acoustic content of the received audio input, wherein detecting the occurrence of a trigger event comprises detecting that the determined acoustic content matches a particular acoustic template.

8. The method of claim 4, further comprising:
   maintaining a buffer of the received audio input in a data storage, wherein the discontinuous recording comprises recording time segments of the received audio input that is maintained in the data storage, whereby recording discontinuous time segments of the received audio input comprises recording time segments of the audio input that are received before detecting occurrence of the trigger event.

9. The method of claim 1, wherein the discontinuous time segments are irregularly spaced in time.

10. The method of claim 1, wherein the discontinuous time segments are regularly spaced in time.

11. The method of claim 1, wherein the one or more of the recorded discontinuous time segments of the received audio input have time durations that are less than approximately 200 milliseconds.

12. The method of claim 1, wherein each recorded discontinuous time segment of the received audio input is separated in time from other recorded discontinuous time segments of the received audio input by more than approximately 800 milliseconds.

13. A system, comprising:
a hearing prosthesis configured to receive an audio input and to stimulate a physiological system of a recipient in accordance with the received audio input, wherein the received audio input represents an audio environment of the recipient and includes speech; and
a controller configured to perform controller operations comprising:
discontinuously recording the received audio input, wherein the discontinuous recording comprises recording discontinuous time segments of the received audio input without recording portions of the audio input between the discontinuous time segments,
wherein one or more of the discontinuous time segments have time durations that are less than an average duration of words of speech, and whereby omitting from the discontinuous recording the portions of the audio input between the discontinuous time segments reduces intelligibility of the speech in the audio input, and
providing an output based on the discontinuous recording of the audio input.

14. The system of claim 13, wherein the controller is provided in the hearing prosthesis.

15. The system of claim 13, wherein the controller is provided in a device that is separate from the hearing prosthesis, and wherein the hearing prosthesis is configured to transmit the received audio input to the device that is separate from the hearing prosthesis.

16. The system of claim 13, wherein the controller operations further comprise:
detecting occurrence of a trigger event, wherein discontinuously recording the received audio input is performed responsive to detecting the occurrence of the trigger event.

17. The system of claim 16, wherein the controller is provided in a device that is separate from the hearing prosthesis, and wherein the hearing prosthesis is configured to transmit the received audio input to the device that is separate from the hearing prosthesis, the controller operations further comprise:
receiving a user input into the device that is separate from the hearing prosthesis, wherein detecting occurrence of the trigger event comprises determining that the received user input includes a command to set an operational mode of a hearing prosthesis.

18. The system of claim 13, wherein the discontinuous time segments are irregularly spaced in time.

19. The system of claim 13, wherein the one or more of recorded discontinuous time segments of the received audio input have time durations that are less than approximately 200 milliseconds.

20. The system of claim 13, wherein each recorded discontinuous time segment of the received audio input is separated in time from other recorded discontinuous time segments of the received audio input by more than approximately 800 milliseconds.

21. A hearing prosthesis comprising:
a microphone;
a stimulator, wherein the stimulator is configured to stimulate a physiological system of a recipient; and
a controller configured to perform controller operations comprising:
receiving, using the microphone, audio input representing an audio environment and including speech,
stimulating, using the stimulator, the physiological system of the recipient in accordance with the received audio input,
discontinuously recording the received audio input, wherein the discontinuous recording comprises recording discontinuous time segments of the received audio input without recording portions of the audio input between the discontinuous time segments,
wherein one or more of the time periods between the discontinuous time segments have time durations that are greater than a specified minimum interval selected to reduce intelligibility of the speech in the audio input, and
providing an output based on the discontinuous recording of the audio input.

22. The hearing prosthesis of claim 21, wherein the hearing prosthesis comprises a cochlear implant, wherein the stimulator is provided in the cochlear implant, and wherein the stimulator is configured to provide electrical stimulation to a cochlea of the recipient.

23. The hearing prosthesis of claim 21, wherein the controller operations further comprise:
detecting occurrence of a trigger event, wherein discontinuously recording the received audio input is performed responsive to detecting occurrence of the trigger event.

24. The hearing prosthesis of claim 23, wherein the controller operations further comprise:
receiving a user input, wherein detecting occurrence of the trigger event comprises determining that the received user input includes a command to set an operational mode of the hearing prosthesis, and
wherein receiving the user input comprises receiving, into the hearing prosthesis from an external device, an indication related to the user input.

25. The hearing prosthesis of claim 21, wherein the time periods between the discontinuous time segments have variable lengths.

26. The hearing prosthesis of claim 21, wherein the recorded discontinuous time segments of the received audio input have time durations that are less than approximately 200 milliseconds.

27. The hearing prosthesis of claim 21, wherein each recorded discontinuous time segment of the received audio input is separated in time from other recorded discontinuous time segments of the received audio input by more than approximately 800 milliseconds.

\* \* \* \* \*